(12) United States Patent
Sato et al.

(10) Patent No.: US 7,582,427 B2
(45) Date of Patent: Sep. 1, 2009

(54) METHOD OF ESTIMATING DRUG METABOLIC ACTIVITY BY ANALYZING MUTATIONS IN GLUCURONOSYL TRANSFERASE GENE

(75) Inventors: Hiroshi Sato, Kusatsu (JP); Yoshihide Fujiyama, Otsu (JP); Kazuo Yamamoto, Rittoh (JP)

(73) Assignee: National University Corporation Shiga University of Medical Science, Shiga (JP)

( * ) Notice: Subject to any disclaimer, the term of this patent is extended or adjusted under 35 U.S.C. 154(b) by 106 days.

(21) Appl. No.: 10/524,278

(22) PCT Filed: Feb. 13, 2003

(86) PCT No.: PCT/JP03/01475

§ 371 (c)(1),
(2), (4) Date: Mar. 15, 2005

(87) PCT Pub. No.: WO2004/016814

PCT Pub. Date: Feb. 26, 2004

(65) Prior Publication Data

US 2006/0257960 A1 Nov. 16, 2006

(30) Foreign Application Priority Data

Aug. 12, 2002 (JP) ............................. 2002-235029

(51) Int. Cl.
*C07H 21/04* (2006.01)
*C12Q 1/68* (2006.01)
(52) U.S. Cl. .......................... 435/6; 435/91.1; 435/91.2; 536/23.1; 536/24.3
(58) Field of Classification Search ........................ None
See application file for complete search history.

(56) References Cited

U.S. PATENT DOCUMENTS

2003/0092019 A1* 5/2003 Meyer et al. .................... 435/6
2005/0032724 A1* 2/2005 Heinrich et al. ............... 514/44

FOREIGN PATENT DOCUMENTS

JP          2001-50931       2/2001
WO         WO 02/18554 A2   3/2002

OTHER PUBLICATIONS

Gagne et al. (Molecular Pharmacology, vol. 62, No. 3, pp. 608-617, Aug. 16, 2002).*
Ito et al. (Eur. J. Clin. Pharmacol. vol. 58, pp. 11-14, Feb. 16, 2002).*
Huang et al. (Pharmacogenetics, vol. 10, pp. 539-544, 2000).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Kurkela et al. "The interactions between the N-terminal and C-terminal domains of the human UDP-glucuronosyltranserases are partly isoform-specific and may involve both monomers" Biochemical Pharmacology, vol. 68, pp. 2443-2450, 2004.*
Huang et al., "Variations of the bilirubin uridine-diphosphoglucuronosyl transferase 1A1 gene in healthy Taiwanese," Pharmacogenetics, 2000, vol. 10, pp. 539-544.
Ito et al., "Effect of a Conserved Mutation in Uridine Diphosphate Glucuronosyltransferase 1A1 and 1A6 on Glucuronidation of a Metabolite of Flutamide," Eur. J. Clin. Pharmacol., vol. 58, No. 1, pp. 11-14 (2002).
Yamamoto et al., "Contribution of Two Missense Mutations (G71R and Y486D) of the Bilirubin UDP Glycosyltransferase (UGT1A1) Gene to Phenotypes of Gilbert's Syndrome and Crigler-Najjar Syndrome Type II," Biochim. Biophys. Acta., vol. 1406, No. 3, pp. 267-273 (1998).
Ando et al., "Polymorphisms of UDP-Glucuronosyltransferase Gene and Irinotecan Toxicity: A Pharmacogenetic Analysis," Cancer Research, vol. 60, pp. 6921-6926 (2000).
Ando et al., "Polymorphisms and UDP-Glucuronosyltransferase and Pharmacokinetics of Irinotecan," Therapeutic Drug Monitoring, vol. 24, pp. 111-116 (2002).
Owens et al., "The Novel UGT1 Gene Complex Links Bilirubin, Xenobiotics, and Therapeutic Drug Metabolism by Encoding UDP-Glucuronosyltransferase Isozymes With a Common Carboxyl Terminus," Journal of Pharmacokinetics and Biopharmaceutics, vol. 24, No. 5, pp. 491-508 (1996).
Jinno et al., "Glucuronidation of 7-Ethyl-10-Hydroxycamptothecin (SN-38), an Active Metabolite of Irinotecan (CPT-11), by Human UGT1A1 Variants, G71R, P229Q, and Y486D," Drug Metabolism and Disposition, vol. 31, pp. 108-113 (2003).
Gagné et al., "Common Human UGT1A Polymorphisms and the Altered Metabolism of Irinotecan Active Metabolite 7-Ethyl-10-Hydroxycamptothecin (SN-38)," Molecular Pharmacology, vol. 62, pp. 608-617 (2002).
Chang et al., "Metabolism of Flutamide in Diet Control Fischer 344 and Brown Norway x F 344 Rats, and Its Hydroxylation and Conjugation by Human CYP450s and UDP-Glucuronosyltransferases," Journal of Food and Drug Analysis, vol. 8, No. 3, pp. 166-173 (2000).
International Search Report for PCT/JP03/01475 mailed May 6, 2003.
International Preliminary Examination Report for PCT/JP03/01475 mailed Apr. 28, 2005 (English translation).
Ritter et al., "A Novel Complex Locus *UGT1* Encodes Human Bilirubin, Phenol, and Other UDP-Glucuronosyltransferase Isozymes with Identical Carboxyl Termini," The Journal of Biological Chemistry, vol. 267, No. 5, Feb. 15, 1992, pp. 3257-3261.

* cited by examiner

*Primary Examiner*—Jeanine A Goldberg
(74) *Attorney, Agent, or Firm*—Kilyk & Bowersox, P.L.L.C.

(57) ABSTRACT

An object of this invention is to provide a method for assaying, predicting or assessing drug metabolism by effectively detecting (a) mutation(s) in a gene coding for UGT. A gene coding for UGT comprises 5 exons, and since the regions of exons 2 through 5 are common to each isoform of UGT1, by assaying a mutation in the common regions, particularly a mutation in exon 5 region, and further adding the detection of (a) mutation(s) in a plurality of exon regions, mutations of UGT1 gene can effectively assayed. A nucleic acid chip using nucleic acid probes is used as a way of detecting (a) mutation(s).

9 Claims, 4 Drawing Sheets

Figure 1

|  | G71R | | | | P229Q | | | | Y486D | | | |
|---|---|---|---|---|---|---|---|---|---|---|---|---|
|  | A | C | G | T | A | C | G | T | A | C | G | T |
|  | ● | ● | ● | ● | ● | ● | ● | ● | ● | ● | ● | ● |
|  | ● | ● | ● | ● | ● | ● | ● | ● | ● | ● | ● | ● |
|  | ● | ● | ● | ● | ● | ● | ● | ● | ● | ● | ● | ● |
|  | ● | ● | ● | ● | ● | ● | ● | ● | ● | ● | ● | ● |
|  | ● | ● | ● | ● | ● | ● | ● | ● | ● | ● | ● | ● |

Figure 2

|  | G71R | | | | P229Q | | | | Y486D | | | |
|---|---|---|---|---|---|---|---|---|---|---|---|---|
|  | A | C | G | T | A | C | G | T | A | C | G | T |
|  | ● | ● | ○ | ● | ● | ○ | ● | ● | ● | ● | ● | ○ |
|  | ● | ● | ○ | ● | ● | ○ | ● | ● | ● | ● | ● | ○ |
|  | ● | ● | ○ | ● | ● | ○ | ● | ● | ● | ● | ● | ○ |
|  | ● | ● | ○ | ● | ● | ○ | ● | ● | ● | ● | ● | ○ |
|  | ● | ● | ○ | ● | ● | ○ | ● | ● | ● | ● | ● | ○ |

● : NO HYBRIDIZATION    ○ : HYBRIDIZATION

Figure 3

● : NO HYBRIDIZATION    ○ : HYBRIDIZATION

Figure 4

● : NO HYBRIDIZATION    ○ : HYBRIDIZATION

Figure 5

|  | G71R | | | | P229Q | | | | Y486D | | | |
|---|---|---|---|---|---|---|---|---|---|---|---|---|
|  | A | C | G | T | A | C | G | T | A | C | G | T |
|  | ○ | ● | ● | ● | ● | ○ | ● | ● | ● | ● | ● | ○ |
|  | ○ | ● | ● | ● | ● | ○ | ● | ● | ● | ● | ● | ○ |
|  | ○ | ● | ● | ● | ● | ○ | ● | ● | ● | ● | ● | ○ |
|  | ○ | ● | ● | ● | ● | ○ | ● | ● | ● | ● | ● | ○ |
|  | ○ | ● | ● | ● | ● | ○ | ● | ● | ● | ● | ● | ○ |

● : NO HYBRIDIZATION     ○ : HYBRIDIZATION

Figure 6

|  | G71R | | | | P229Q | | | | Y486D | | | |
|---|---|---|---|---|---|---|---|---|---|---|---|---|
|  | A | C | G | T | A | C | G | T | A | C | G | T |
|  | ● | ● | ○ | ● | ○ | ○ | ● | ● | ● | ● | ● | ○ |
|  | ● | ● | ○ | ● | ○ | ○ | ● | ● | ● | ● | ● | ○ |
|  | ● | ● | ○ | ● | ○ | ○ | ● | ● | ● | ● | ● | ○ |
|  | ● | ● | ○ | ● | ○ | ○ | ● | ● | ● | ● | ● | ○ |
|  | ● | ● | ○ | ● | ○ | ○ | ● | ● | ● | ● | ● | ○ |

● : NO HYBRIDIZATION     ○ : HYBRIDIZATION

Figure 7

|  | G71R | | | | P229Q | | | | Y486D | | | |
|---|---|---|---|---|---|---|---|---|---|---|---|---|
|  | A | C | G | T | A | C | G | T | A | C | G | T |
|  | ● | ● | ○ | ● | ● | ○ | ● | ● | ● | ● | ○ | ○ |
|  | ● | ● | ○ | ● | ● | ○ | ● | ● | ● | ● | ○ | ○ |
|  | ● | ● | ○ | ● | ● | ○ | ● | ● | ● | ● | ○ | ○ |
|  | ● | ● | ○ | ● | ● | ○ | ● | ● | ● | ● | ○ | ○ |
|  | ● | ● | ○ | ● | ● | ○ | ● | ● | ● | ● | ○ | ○ |

● : NO HYBRIDIZATION    ○ : HYBRIDIZATION

Figure 8

|  | G71R | | | | P229Q | | | | Y486D | | | |
|---|---|---|---|---|---|---|---|---|---|---|---|---|
|  | A | C | G | T | A | C | G | T | A | C | G | T |
|  | ● | ● | ○ | ● | ● | ○ | ● | ● | ● | ● | ○ | ● |
|  | ● | ● | ○ | ● | ● | ○ | ● | ● | ● | ● | ○ | ● |
|  | ● | ● | ○ | ● | ● | ○ | ● | ● | ● | ● | ○ | ● |
|  | ● | ● | ○ | ● | ● | ○ | ● | ● | ● | ● | ○ | ● |
|  | ● | ● | ○ | ● | ● | ○ | ● | ● | ● | ● | ○ | ● |

● : NO HYBRIDIZATION    ○ : HYBRIDIZATION

METHOD OF ESTIMATING DRUG METABOLIC ACTIVITY BY ANALYZING MUTATIONS IN GLUCURONOSYL TRANSFERASE GENE

This application is a National Stage Application of PCT/JP2003/01475, filed Feb. 13, 2003, which claims priority from Japanese Patent Application No. 2002-235029, filed Aug. 12, 2002.

TECHNICAL FIELD

The present invention relates to a method used in the field of clinical testing, in particular to a method for assaying genes of an enzyme involved in glucuronidation, and probes and a kit used therefor.

BACKGROUND ART

Uridine diphosphate glucuronosyltransferases (UDP-glucuronosyltransferases, UGT) are enzymes that catalyze glucuronidation of various drugs. UGTs are grouped into two families, UGT1 and UGT2, based on the homology of their amino acid sequences.

At least 9 isoforms are known to exist for UGT1, that is, UGT1A1 and UGT1A3 to UGT1A10. For example, UGT1A1 conjugates bilirubin, amine, phenol and the like, while UGT1A6 conjugates phenol that has a planar molecular structure. Human UGT1 gene (UGT1) is present on the chromosome 2q37 and comprises an exon 1 that is substrate specific for each isoform (1A1 to 1A10) and exons 2 to 5 that are common for all isoforms, and has a promoter region including a TATA box that is present upstream of each exon 1. The isoforms have the irrespective unique amino terminal regions that are encoded by one of at least nine exons in the first exon group, and a common carboxyl terminal region that is encoded by 4 exons.

Meanwhile, UGT2 is grouped into the subfamilies of UGT2A that conjugates odorants and UGT2 that conjugates bile acids and steroids.

Jaundices for which a clear cause (observation of hemolysis etc.) is not found and which exhibit no abnormality other than a high serum bilirubin value in a standard liver function test are referred to as "constitutional jaundices" and are broadly classified into Crigler-Najjar syndrome type I and type II and Gilbert syndrome in which indirect (unconjugated type) bilirubin rises in level, and Dubin-Johnson syndrome and Rotor syndrome in which direct (conjugated type) bilirubin rises in level. It has been reported that a mutation occurs in exon 5 of UGT1A1 gene in Crigler-Najjar syndrome type I and type II and Gilbert syndrome. More specifically, due to a mutation (Y486D) in which tyrosine is replaced with aspartic acid at position 486 in the amino acid sequence, the enzyme activity drops to $1/13$th that of the normal enzyme.

Meanwhile, cytochrome P450 is well known as a substance involved in drug metabolism in the body. It is also well known that due to differences in polymorphisms of this enzyme a specific drug may not be metabolized to cause abnormality in drug metabolism. Abnormalities in drug metabolism are caused not only by polymorphisms of cytochrome P450. Since a drug undergoes glucuronidation to be metabolized as described above, it has been known that polymorphisms of UGT are involved in drug metabolism. However, with respect to the relation between polymorphisms of UGT and the metabolism of various drugs, an available mutation of genes that can reflect metabolism for a large number of drugs is unclear. In particular, the relation between mutations of the exon 5 region of UGT1 gene and drug metabolism is unclear.

DISCLOSURE OF THE INVENTION (Problem to be Solved)

It is an object of the present invention to provide a method for assessing, predicting or assaying drug metabolism by effectively detecting a mutation of a gene coding for UGT.

(Means for Solving the Problem)

As the result of concentrated research the present inventors found that, since a gene coding for UGT comprises five exons of which the regions of exons 2 to 5 are common to the isoforms of UGT1, it has been recognized that by investigating mutations of these regions, especially by detecting (a) mutation(s) in the exon 5 region of the UGT1 molecule, mutations in UGT1 can be effectively detected without conducting assay for each UGT1 isoform, which allows efficient prediction of drug metabolism. The finding thus completes the present invention.

More specifically, this invention comprises the following.

1. An assay method for drug metabolizing activity of UDP-glucuronosyltransferase (UGT), comprising a step of detecting (a) mutation(s) in an exon 5 region of a gene coding for UGT.
2. The assay method according to the preceding 1, further comprising a step of detecting (a) mutation(s) of an increase or decrease in the repeating sequence of TA present in a TATA box of a promoter region.
3. The assay method according to the preceding 1 or 2, wherein the method comprises a step of detecting (a) mutation(s) in an exon 5 region having a nucleotide sequence that is common to each isoform of UGT1A1, UGT1A3, UGT1A4, UGT1A5, UGT1A6, UGT1A7, UGT1A8, UGT1A9 and UGT1A10 for a sample including a gene coding for UGT1, without conducting an assay for each of the isoforms.
4. The assay method according to the preceding 3, comprising a step of detecting (a) mutation(s) in the exon 5 region of each isoform of UGT1A molecule, that correspond(s) to nucleotide number 1456 in the genetic sequence of UGT which encodes an amino acid at position 486 in the amino acid sequence of UGT1A1 molecule.
5. The assay method according to any one of the preceding 1 to 4, comprising, in addition to the step of detecting the mutation(s), a step of detecting (a) mutation(s) in at least one region of the regions of exons 1, 2, 3, and 4 of a genetic sequence coding for a UGT molecule.
6. The assay method according to the preceding 5, comprising a step of detecting at least one genetic sequence mutation of a mutation at nucleotide number 226 in a genetic sequence of UGT coding for an amino acid at position 71 in the amino acid sequence of UGT1A1 molecule and a mutation at nucleotide number 486 in a genetic sequence coding for an amino acid at position 229 in the amino acid sequence of UGT1A1 molecule.
7. A UGT gene having (a) mutation(s) comprising the base substitution described in the preceding 3 or 4, or a gene fragment including the mutation(s).
8. DNA fragments having a functionally effective length as assayed DNA that are provided for the detection method for a base substitution described in any one of the preceding 1 to 6, or DNA fragments having a functionally effective length as probes for use in the detection method for a base substitution described in any one of the preceding 1 to 6.

9. The DNA fragments according to the preceding 7 or 8, which are oligonucleotide probes that are specific to UGT having a base sequence set forth in any one of SEQ ID NOS: 1 to 3.
10. The assay method according to the preceding 5 or 6, which uses a combination of probes having a base sequence set forth in SEQ ID NO: 1 and probes having a base sequence set forth in SEQ ID NO: 2 and/or 3.
11. A detection device in which the oligonucleotide probes according to any one of the preceding 7 to 9 or the oligonucleotide probes used for the method according to the preceding 10 are provided within the same device.
12. The detection device according to the preceding 11, which is a nucleic acid array or a nucleic acid chip in which an end of the base sequence of the oligonucleotide probes according to any one of the preceding 7 to 9 is immobilized by bonding to an insoluble support via a functional group.
13. A method for assessing, predicting or assaying drug metabolism using the device according to the preceding 11 or 12.
14. An assay kit used in the method according to any one of the preceding 1 to 6, 10 and 13, which includes the nucleic acid fragments according to any one of the preceding 7 to 9 or the device according to the preceding 11 or 12.

DESCRIPTION OF THE PREFERRED EMBODIEMNT

Hereunder this invention is described in detail by way of embodiments.
The 2-amino-5-nitro-4-trifluoromethylphenol glucuronide conjugate is a principal metabolite of flutamide, which is a nonsteroidal antiandrogenic drug used to treat prostatic cancer and has strong hepatotoxicity.
2-amino-5-nitro-4-trifluoromethylphenol is glucuronidated by UGT. The enzymatic reactions in glucuronidation by the enzymes of each of the isoforms UGT1A1 and UGT1A6 between their normal molecules and molecules with Y486D mutation were compared, respectively. The results showed that the UGT1A1 mutant had a maximum velocity of about 12% relative to the maximum velocity of the wild type, and had a Km value which was about half of that of the wild type with respect to 2-amino-5-nitro-4-trifluoromethylphenol and equal to that of the wild type with respect to UDP-glucuronate. In contrast, the UGT1A6 mutant exhibited less than 1% of the activity of the wild type, and the maximum velocity and Km value were both at levels at which measurement was not possible.
As mentioned in the foregoing, since UGT1gene has regions of exons 2 through 5 that are common for each isoform and an exon 1 region that differs for each isoform, it can be said that when mutations occur in the common exon regions the UGT1 enzyme activity will decrease for all the isoforms.

By investigating mutations in the common exon regions, this invention provides a method for effectively assaying genetic mutations for all isoforms that can be present for UGT1. More specifically, for example, by assaying a mutation (Y486D) in the exon 5 region of UGT1A1 and UGT1A6 it is possible to predict drug metabolism by these enzymes.
Further, by adding a step of detecting mutations in the exon 1 region of UGT1 to detect mutations that are unique to each isoform, and combining these, this invention can provide an assay method for mutations of UGT gene that enables a comprehensive reduction in the frequency of omissions in detecting mutations of UGT gene. It is thus possible to provide a method for conducting effective assay and prediction of drug metabolism.
This invention discloses an assay method for (a) mutation(s) in the exon5 region of UGT1A1, more specifically, a Y486D mutation, and the assay method allows to detect the simultaneously occurring mutations in other isoforms. For example, the same probes and/or the same device can be used to assay a Y487D mutation that is a mutation of UGT1A3, UGT1A4 and UGT1A5, a Y485D mutation that is a mutation of UGT1A6, and a Y483D mutation that is a mutation of UGT1A7, UGT1A8, UGT1A9 and UGT1A10, etc. Therefore, according to the method of this invention, it is possible to detect mutations in the exon 5 regions of all of these isoforms using one kind of nucleic acid probes without having to individually assaying mutations for each of the isoforms of UGT1A that plays an important role in drug metabolism, thus enabling the assessment, prediction-or assay for drug metabolism by a decrease in the enzyme activity.
Further, by detecting an increase or decrease in TA sequence repetitions present in a TATA box that is present in the promoter region of UGT gene, detection of the drug metabolizing activity of UGT can be carried out with greater accuracy. Normally, the TA sequence is repeated 6 times in the region of a TATA box. However, when the number of TA sequence repetitions increases or decreases it influences the drug metabolizing activity of UGT. Thus, the drug metabolizing activity of UGT can be assayed by detecting mutations relating to an increase or decrease in the number of TA sequence repetitions. More specifically, the drug metabolizing activity of UGT can be assayed by detecting mutations in which the number of sequence repetitions is any one number from 4 to 8 and a combination of any numbers from 4 to 8 in the case of heterozygotes, and mutations in which the number is 4, 5, 7 or 8 in the case of homozygotes. A method for detecting mutations relating to an increase or decrease in the number of TA sequence repetitions in a TATA box can be carried out according to a known method.
Since a genetic mutation to be detected is clarified and specified in this invention by following the disclosure of the invention, it will be easy for a person skilled in the art to suitably apply the method for the detection of the mutation or to apply the method after modifying it appropriately. For example, when taking as a target a UGT gene of a tested subject, detection of the specific mutation of this invention (Y486Dmutation) can be conducted according to various methods for analyzing a base sequence that includes the mutation site. Examples of such methods include Southern hybridization, dot hybridization (J. Mol. Biol., 98: 503-517, 1975, etc.), dideoxy sequencing, and various detection methods that combine DNA amplification techniques [for example, polymerase chain reaction (PCR)-restriction fragment length polymorphism (RFLP) analysis, PCR-single strand higher-order structure polymorphism analysis (Proc. Natl. Acad. Sci., U.S.A., 86: 2766-2770, 1989, etc.), PCR-specific sequence oligonucleotide (SSO) analysis, and an allele-specific oligonucleotide technique using PCR-SSO and dot hybridization (Nature, 324: 163-166, 1986 etc.)]. It is also possible to conduct simple and easy detection with a nucleic acid array or nucleic acid chip using an oligonucleotide probe.

(Probe)

For a gene encoding UGT1 molecule, a mutation (G71R) at nucleotide number 226 in exon 1, a mutation (P229Q) at nucleotide number 686 in exon 1 and a mutation (Y486D) at nucleotide number 1456 in exon 5 can be detected using nucleic acid probes.

The number of nucleotides in DNA fragments for these nucleic acid probes is at least 8, normally within the range of 10 to 50, and preferably from 15 to 30. If the number of nucleotides of a probe exceeds the aforementioned numbers by too many counts, it will be difficult for the probe to hybridize to single-strand DNA, and if the number of nucleotides is too small the hybridization specificity will decrease.

More specifically, an oligonucleotide having the base sequence TCAGAGACNGAGCATTTT (SEQ ID NO: 2) can be used as a probe for detecting a G71R mutation, an oligonucleotide having the base sequence TAATTCCCNGTATGAAA (SEQ ID NO: 3) can be used as a probe for detecting a P229Q mutation, and an oligonucleotide having the base sequence TGGTACCAGNACCATTCCT (SEQ ID NO: 1) can be used as a probe for detecting a Y486D mutation. In this case, N represents a universal base such as inosine or any of A, T, C and G.

Required chemical substances can also be added to the ends of these oligonucleotides, for example, a substance to facilitate spotting when preparing a nucleic acid array or various labelling substances or the like.

According to this invention, the probe is not limited to a DNA fragment having a base sequence set forth in the aforementioned SEQ ID NOS: 1 to 3, and includes any probe that is just capable of functioning as a probe for detection of UGT gene, even if it has a small number of mismatches with a template strand. For example, the probe may comprise a sequence that has been modified by, for example, a substitution, deletion and/or addition of upto 2 nucleotides in a base sequence set forth in the aforementioned SEQ ID NOS: 1 to 3, as long as it has the aforementioned functions as a probe.

Each of the aforementioned oligonucleotides employed as probes for use in this invention can be easily synthesized using an automatic synthesizer, for example, DNA synthesizer (Perkin-Elmer Inc.), in accordance with an ordinary method, and obtained oligonucleotides can also be purified using a commercially available purification cartridge etc. according to necessity. In order to apply the synthetic oligonucleotides to a nucleic acid array in which they are immobilized on the surface of a slide glass, the 5'-ends thereof are also preferably labeled with an amino.

(Nucleic Acid Array)

Each of the above probes can be immobilized to the surface of a slide glass or the like for use as a nucleic acid array (also generally referred to as a "microarray") A known method can be applied for preparing the nucleic acid array, and the method is not particularly limited (e.g., see "Idenshi Kogaku Jikken Noto Shita" (Genetic Engineering Experiment Notes, The last volume), published by Yodosha Co., Ltd., 175-187 (2002)). For example, the array can be prepared by spotting on a slide glass coated with aminosilane using the commercially available arrayer, Affymetrix 417 arrayer.

(Preparation of Target Sample and Assay Sample)

According to the method of this invention, it is possible to easily assess drug metabolism by glucuronidation that occupies an important position in kinetic studies for drug development. Thereby, the suitability with which a drug can be administrated to be metabolized can be determined. A sample to be used as a measurement target is not particularly limited as long as it is a biological sample, and for example, tissue or organs such as liver, kidney, leukocyte or hair may be mentioned. When the expression amount of UGT gene in a measurement sample is small, the sample in which a target nucleic acid has been amplified by an appropriate amplification method such as PCR, LAMP, LCR or NASBA can be measured.

An assay sample can be prepared by extracting DNA from the target sample for assay and amplifying the DNA by, for example, PCR, using a pair of primers that are specific to a region in which (a) mutation(s) is(are) to be detected. More specifically, a primer labeled with fluorescence at the 5'-end (for example, 5'-Cy3-labeled oligo-DNA) can be used to prepare the fluorescence-labeled sample, which is in turn hybridized with the probe on a nucleic acid array to detect directly the hybridization result.

As the primer for use in sample preparation, for example, the following primers can be used. Thus, fluorescence-labeled samples can be prepared by amplifying the DNAs.

```
1) Primer pair for detecting mutation site G71R:
G71R-F
(CTGCAGCAGAGGGGACATGA)          (SEQ ID NO: 4)

Cy3-G71R-R
(Cy3-AACATTATGCCCGAGACTAAC)     (SEQ ID NO: 5)

2) Primer pair for detecting mutation site P229G:
P229Q-F
(CAACCCATTCTCCTACGTG)           (SEQ ID NO: 6)

Cy3-P229G-R
(Cy3-AGATGCAGAGCTCAATAGGTC)     (SEQ ID NO: 7)

3) Primer pairs for detecting mutation site Y486D:
a) Y486D-F
(GCTGGACCTGGCAGTGTTC)           (SEQ ID NO: 8)

Cy3-Y486D-R
(Cy3-TTTCCGGTAGCCATATGCACA)     (SEQ ID NO: 9)

b) Y486D-F2
(CCGCAGCCCACGACCTCACCTGGT)      (SEQ ID NO: 10)

Cy3-Y486D-R2
(Cy3-AGAGGAAACCAATCACGTCCAAGG)  (SEQ ID NO: 11)
```

(Detection)

A commercially available detector can be used to detect the aforementioned fluorescence labels on a nucleic acid array. For example, the fluorescence signal of each spot can be detected by scanning using an Affymetrix 428 Array Scanner.

(Target Drugs)

As long as drugs to be assayed by the method of this invention are glucuronidated by UGT, they are useful for assay of their metabolisms. Examples of these drugs include diuretic agents such as spironolactone, analgesics such as acetaminophen, aspirin, floctafenine and indomethacin, psychotropic drugs such as haloperidol, carpipramine, lorazepam and amoxapine, anesthetic analgesics such as morphine, propofol and opium, the anticancer agent such as doxorubicin hydrochloride, the antitussive agent such as codeine phosphate, the antiasthmatic agent such as orciprenaline sulfate, the antiepileptic drug such as phenytoin, the antihistamine such as ketotifen fumarate, hypotensive agents and therapeutic agents for angina pectoris such as carvedilol and propranolol hydrochloride, the lipid metabolism improving agent such as aluminium clofibrate, and the therapeutic agent for Alzheimer's disease such as donepezil hydrochloride.

EXAMPLES

Hereunder, the present invention is illustrated in further detail by the following examples. However, the invention is not limited to these examples.

Example 1

Preparation of Nucleic Acid Array

Figure 1:
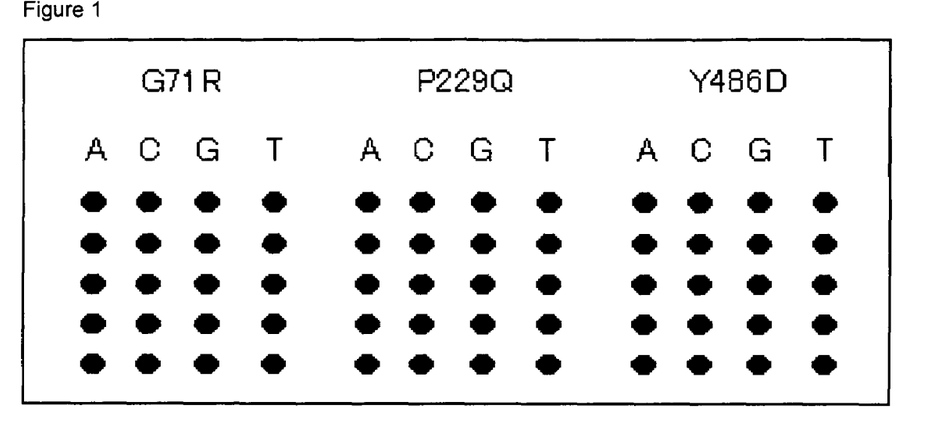
FIG. 1 is a view showing the layout of nucleic acid probes on a DNA chip.

DNA chips were prepared by synthesizing 5'-amino modified oligonucleotides having the respective sequences set forth in SEQ ID NOS: 1 to 12 and then spotting the oligonucleotides on the surface of an aminosilane-coated slide glass (Sigma Inc.) using an Affymetrix 417 Arrayer. Five oligonucleotides were spotted for each kind of synthesized oligonucleotide. FIG. 1 shows the spot layout of the prepared array.

Example 2

Preparation of Samples

Fluorescence-labeled samples were prepared by amplifying 7 kinds of assay samples by PCR using as primers the 5'-Cy3-labeled oligonucleotides and unlabelled oligonucleotides described hereafter. A PCR amplification product of 150 base pairs was obtained using G71R-F and Cy3-G71R-R as a primer pair for detecting mutation site G71R, a PCR amplification product of 195 base pairs was obtained using P229Q-F and Cy3-P229G-R as a primer pair for detecting mutation site P229G, and a PCR amplification product of 187 base pairs was obtained using Y486D-F and Cy3-Y486D-R as a primer pair for detecting mutation site Y486D. The PCR conditions were as follows:

| Reaction volume | 100 μL |
| --- | --- |
| Template | 1 μL of assay sample |
| Primers | 20 pmol each |
| Enzyme used | Ex Taq |
| Reaction conditions | 94° C.-30 secs |
| | 55° C.-30 secs |
| | 72° C.-30 secs |
| | 35 cycles |

The reaction products were purified by ethanol precipitation.

Example 3

Hybridization and Detection

Each sample prepared in Example 2 was dissolved in 12 μL of hybridization buffer [4×SSC ("4×" represents a fourfold concentration of a original solution of 0.15 mol/L of NaCl and 15 mmol/L of sodium citrate), 0.2% SDS, 50% formamide], and 10 μL thereof was then hybridized for 2 hrs at 42° C. to the nucleic acid array prepared in Example 1. After hybridization, the array was washed with buffer (2×SSC, 0.2% SDS) for 5 min at 37° C., washed again with buffer (0.2×SSC) for 5 min at room temperature and dried, after which fluorescence signals were detectedusing an Affymetrix 428 Array Scanner. The results are shown in FIGS. 2 to 8.

Figure 2:
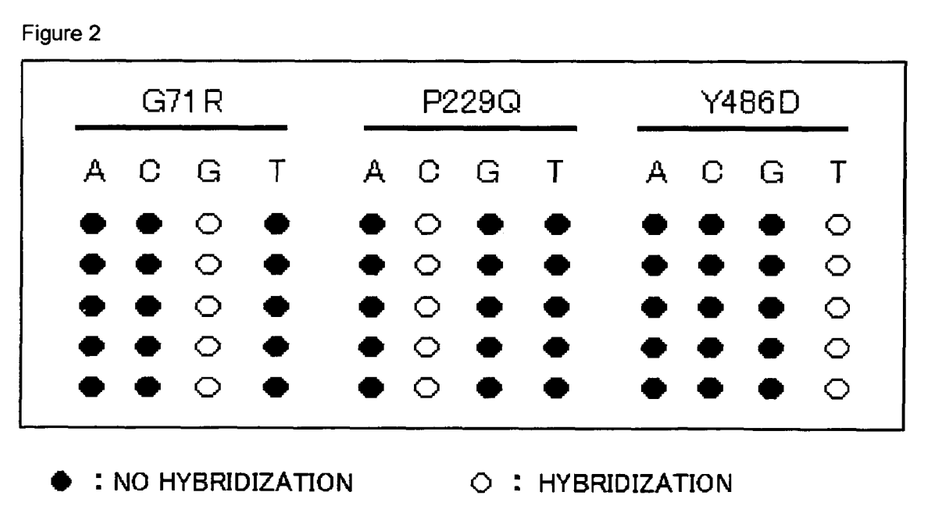
FIG. 2 is a view showing the assay result for sample 1 (normal specimen).

For sample 1, hybridization was observed respectively in only the G column of the G71R mutation detection chip, only the C column of the P229Q mutation detection chip, and only the T column of the Y486D mutation detection chip. This indicated that each of these had a normal sequence (FIG. 2).

Figure 3:
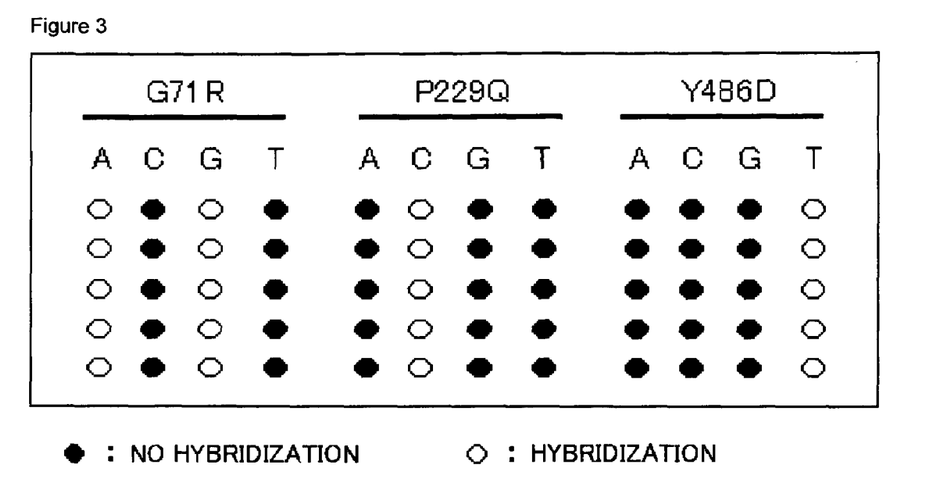
FIG. 3 is a view showing the assay result for sample 2.
Figure 4:
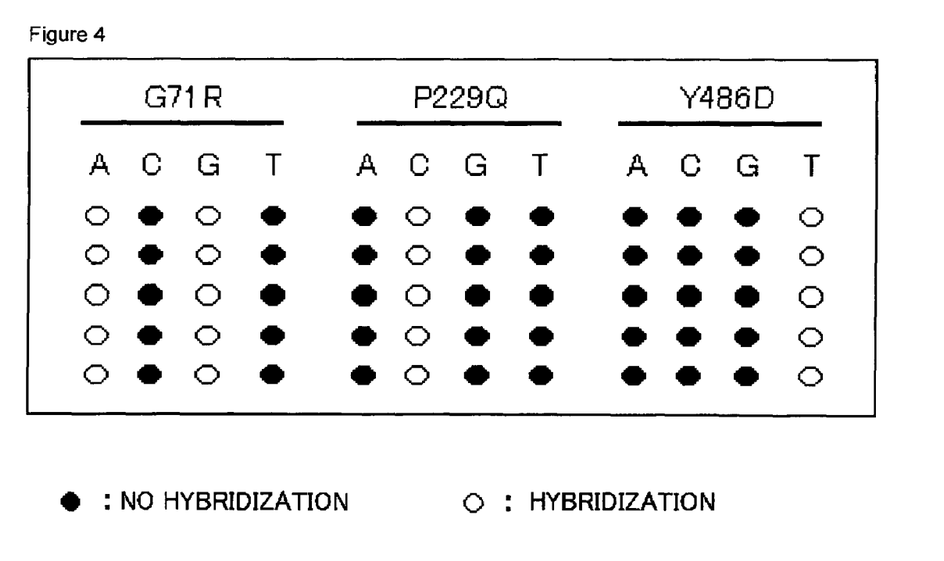
FIG. 4 is a view showing the assay result for sample 3.

For samples 2 and 3, while hybridization was observed in the C column of the P229Q mutation detection chip and the T column of the Y486D mutation detection chip to indicate that each had a normal sequence, hybridization was observed in both the A column and the G column of the G71R mutation detection chip. Thus, a heterozygous mutation having both a normal sequence hybridizing to the G column and a mutation sequence hybridizing to the A column was confirmed (FIG. 3, FIG. 4).

Figure 5:
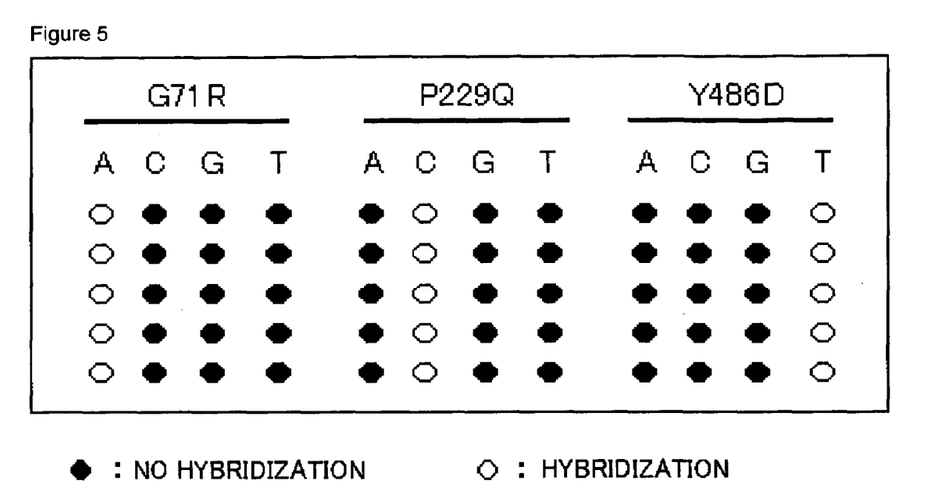
FIG. 5 is a view showing the assay result for sample 4.

For sample 4, while normal hybridization was observed for both the P229Q and Y486D mutation detection chips, hybridization was observed in only the A column for the G71R mutation detection chip. Thus, a homozygous mutation was confirmed (FIG. 5).

Figure 6:
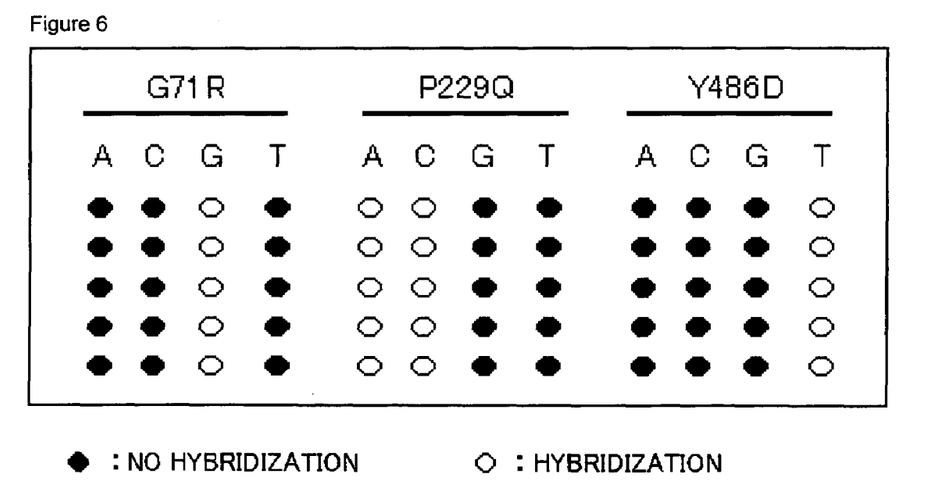
FIG. 6 is a view showing the assay result for sample 5.

For sample 5, while hybridization was normal in both the G71R and Y486D mutation detection chips, in the P229Q chip, hybridization was observed in the C column indicating normal hybridization and also in the A column. Thus, a heterozygous mutation was confirmed (FIG. 6).

Figure 7:
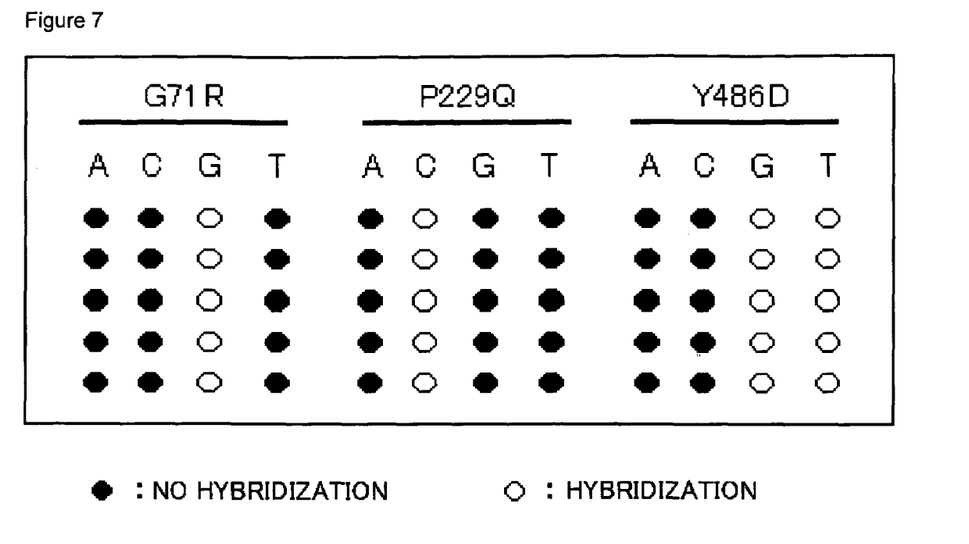
FIG. 7 is a view showing the assay result for sample 6.

For sample 6, while normal hybridization was observed for both the G71R and P229Q mutation detection chips, for the Y486D mutation detection chip, hybridization was observed in the T column indicating normal hybridization and also in the G column indicating mutation. Thus, a heterozygous mutation was confirmed (FIG. 7).

Figure 8:
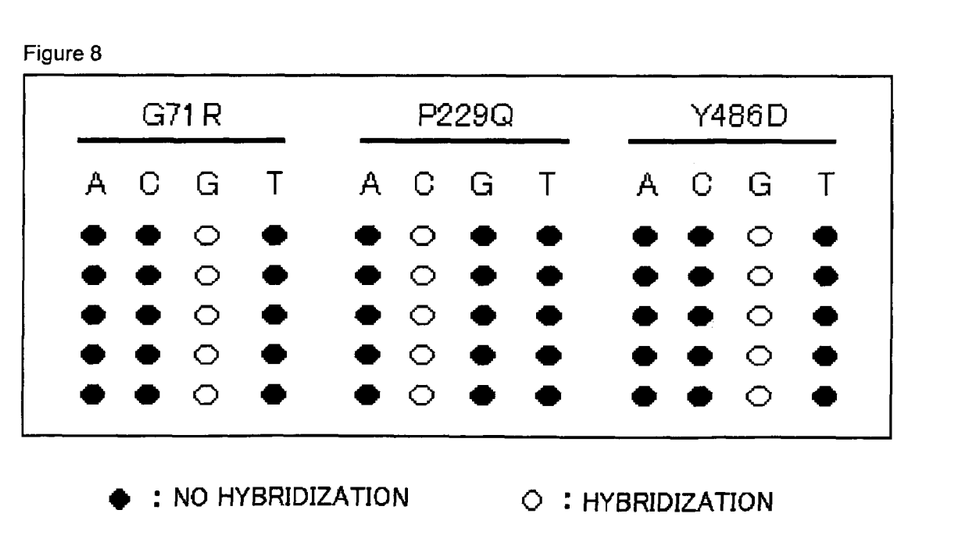
FIG. 8 is a view showing the assay result for sample 7.

For sample 7, in contrast to sample 6, hybridization was observed in only the G column for the Y486D mutation detection chip. Thus, a homozygous mutation was confirmed (FIG. 8).

UGT molecules derived from the same genetic sequences as the above 7 kinds of samples were prepared by genetic recombination, and after comparing the above results with results for the UGT activity thereof measured by using bilirubin as a substrate, as shown in Table1, it was confirmed that detection of a mutation in an exon 5 region encoding a UGT molecule, particularly a Y486D mutation, makes it possible to predict the enzyme activity of the UGT molecule. This showed that it is possible to assay an abnormality of drug metabolism. Further, it was shown that an abnormality of drug metabolism can be assayed for more effectively by combining this detection with detection of (a) mutation(s) in the regions of exons 1 to 4 other than the exon 5 region.

TABLE 1

DNA chip analysis result and UGT activity of corresponding UGT1A1 molecule produced by genetic recombination

| UGT gene mutation | UGT relative activity (glucronidation activity) |
| --- | --- |
| normal | 100% |
| G71R (homozygous) | 32% |
| G71R (heterozygous) | 60% |
| P229Q (heterozygous) | 15% |
| Y486D (homozygous) | 8% |
| Y486D (heterozygous) | 36% |

Example 4

For a UGT1A6 molecule for which a mutation in the exon 5 region was detected in a similar manner to Example 1, the result of analysis of the mutation in the exon 5 region was compared with UGT activity of the UGT1A6 molecule corresponding thereto produced by genetic recombination, that was measured using 2-amino-5-nitro-4-trifluoromethylphenol as a substrate. The result is shown in Table 2.

TABLE 2

DNA chip analysis result and UGT activity of corresponding UGT1A1 molecule produced by genetic recombination

| UGT gene mutation | UGT relative activity (glucronidation activity) |
|---|---|
| normal | 100% |
| Y485D (homozygous) | >1% |

It was thus shown that (a) mutation(s) of not only UGT1A1 but also other isoforms can be detected by the method of this invention, thereby confirming the effectiveness of this invention.

INDUSTRIAL APPLICABILITY

As described in the foregoing, according to the method of this invention for detecting (a) mutation(s) in common exon regions coding for UGT1, it is possible to effectively detect (a) mutation(s) of UGT1gene without the need to assay individually each of the large number of isoforms thereof, enabling effective assessment, prediction and assay with respect to the metabolism for a large number of drugs.

The invention claimed is:

1. A method for predicting the level of enzymatic activity of a UGT1A1 or UGT1A6 molecule in 2-amino-5-nitro-4-trifluoromethylphenol drug glucuronidation in a human subject, comprising:
   a) obtaining a nucleic acid sample from said human
   b) detecting a mutation in the exon 5 region of the UGT1A1 or UGT1A6 molecule without conducting an assay for each of the isoforms, that corresponds to nucleotide number 1456 in the genetic sequence of UGT1A1 which encodes an amino acid at position 486 in the amino acid sequence of UGT1A1 molecule and
   c) determining that, when the mutation in the exon 5 region encoding a UGT1A1 or UGT1A6 molecule is detected, the level of enzymatic activity of the UGT1 molecule in drug glucuronidation in the human subject would be lower than that of a UGT1 molecule without the mutation;
   wherein the drug glucuronidation is glucuronidation of 2-amino-5-nitro-4-trifluoromethylphenol.

2. The assay method according to claim 1, further comprising a step of detecting (a) mutation(s) of an increase or decrease in the repeating sequence of TA present in a TATA box of a promoter region.

3. The assay method according to claim 1, comprising, in addition to the step of detecting the mutation(s), a step of detecting (a) mutation(s) in at least one region of the regions of exons 1, 2, 3, and 4 of a genetic sequence coding for a UGT1 molecule.

4. The assay method according to claim 3, comprising a step of detecting at least one genetic sequence mutation of a mutation at nucleotide number 226 in a genetic sequence of UGT 1 coding for an amino acid at position 71 in the amino acid sequence of UGT1A1 molecule and a mutation at nucleotide number 686 in a genetic sequence coding for an amino acid at position 229 in the amino acid sequence of UGT1A1 molecule.

5. The assay method according to claim 4, which uses a combination of probes comprising SEQ ID NO: 1 and probes comprising SEQ ID NO: 2 and/or 3.

6. The assay method according to claim 3, which uses a combination of probes comprising SEQ ID NO: 1 and probes comprising SEQ ID NO: 2 and/or 3.

7. A method for assessing, predicting or assaying drug glucuronidation in a human subject comprising:
   a) using a detection device in which probes comprising SEQ ID NO: 1 and probes comprising SEQ ID NO: 2 and/or 3 are provided within the same device to detect a mutation in an exon 5 region of a gene coding for UGT1A1 or UGT1A6, having a nucleotide sequence that is common to each isoform of UGT1A1 and UGT1A6, that correspond(s) to nucleotide number 1456 in the genetic sequence of UGT1 which encodes an amino acid at position 486 in the amino acid sequence of UGT1A1 molecule; and
   b) determining that, when the mutation in an exon 5 region encoding a UGT1A1 or UGT1A6 molecule is detected, the level of enzymatic activity of the UGT1A1 or UGT1A6 molecule in drug glucuronidatiion in the subject would be lower than that of a UGT1 molecule without the mutation
   wherein the drug glucuronidation is glucuronidation of 2-amino-5-nitro-4-trifluoromethylphenol.

8. An assay method for drug glucuronidation of UDP-glucuronosyltransferase 1A1 or 1A6 (UGT1A1 or UGT1A6) of a subject, wherein the subject is human, comprising:
   a) detecting (a) mutation(s) in an exon 5 region of a gene coding for UGT1A1 or UGT1A6, having a nucleotide sequence that is common to each isoform of UGT1A1 and UGT1A6, by using a combination of probes comprising SEQ ID NO: 1 and probes comprising SEQ ID NO: 2 and/or 3, and
   b) determining that, when the mutation in an exon 5 region encoding a UGT1A1 or UGT1A6 molecule is detected, the level of enzymatic activity of the UGT1A1 or UGT1A6 molecule in drug glucuronidation in the subject would be lower than that of a UGT1 molecule without the mutation
   wherein the drug glucuronidation is glucuronidation of 2-amino-5-nitro-4-trifluoromethylphenol.

9. The assay method according to claim 8, further comprising a step of detecting (a) mutation(s) of an increase or decrease in the repeating sequence of TA present in a TATA box of a promoter region.

* * * * *

SEQUENCE LISTING

<160> NUMBER OF SEQ ID NOS: 11

<210> SEQ ID NO 1
<211> LENGTH: 19
<212> TYPE: DNA
<213> ORGANISM: Artificial
<220> FEATURE:
<223> OTHER INFORMATION: Designed DNA based on UGT1 gene
<220> FEATURE:
<221> NAME/KEY: misc_feature
<222> LOCATION: (10)..(10)
<223> OTHER INFORMATION: N is universal base such as A, T, C, G or
      inosine

<400> SEQUENCE: 1
tggtaccagn accattcct                                                19

<210> SEQ ID NO 2
<211> LENGTH: 18
<212> TYPE: DNA
<213> ORGANISM: Artificial
<220> FEATURE:
<223> OTHER INFORMATION: Designed DNA based on UGT1 gene
<220> FEATURE:
<221> NAME/KEY: misc_feature
<222> LOCATION: (9)..(9)
<223> OTHER INFORMATION: N is universal base such as A, T, C, G or
      inosine

<400> SEQUENCE: 2
tcagagacng agcatttt                                                 18

<210> SEQ ID NO 3
<211> LENGTH: 17
<212> TYPE: DNA
<213> ORGANISM: Artificial
<220> FEATURE:
<223> OTHER INFORMATION: Designed DNA based on UGT1 gene
<220> FEATURE:
<221> NAME/KEY: misc_feature
<222> LOCATION: (9)..(9)
<223> OTHER INFORMATION: N is universal base such as A, T, C, G or
      inosine

<400> SEQUENCE: 3
taattcccng tatgaaa                                                  17

<210> SEQ ID NO 4
<211> LENGTH: 20
<212> TYPE: DNA
<213> ORGANISM: Artificial
<220> FEATURE:

<223> OTHER INFORMATION: Designed DNA based on UGT1 gene

<400> SEQUENCE: 4
ctgcagcaga ggggacatga                                         20

<210> SEQ ID NO 5
<211> LENGTH: 21
<212> TYPE: DNA
<213> ORGANISM: Artificial
<220> FEATURE:
<223> OTHER INFORMATION: Designed DNA based on UGT1 gene

<400> SEQUENCE: 5
aacattatgc ccgagactaa c                                       21

<210> SEQ ID NO 6
<211> LENGTH: 19
<212> TYPE: DNA
<213> ORGANISM: Artificial
<220> FEATURE:
<223> OTHER INFORMATION: Designed DNA based on UGT1 gene

<400> SEQUENCE: 6
caacccattc tcctacgtg                                          19

<210> SEQ ID NO 7
<211> LENGTH: 21
<212> TYPE: DNA
<213> ORGANISM: Artificial
<220> FEATURE:
<223> OTHER INFORMATION: Designed DNA based on UGT1 gene

<400> SEQUENCE: 7
agatgcagag ctcaataggt c                                       21

<210> SEQ ID NO 8
<211> LENGTH: 19
<212> TYPE: DNA
<213> ORGANISM: Artificial
<220> FEATURE:
<223> OTHER INFORMATION: Designed DNA based on UGT1 gene

<400> SEQUENCE: 8
gctggacctg gcagtgttc                                          19

<210> SEQ ID NO 9
<211> LENGTH: 21
<212> TYPE: DNA
<213> ORGANISM: Artificial
<220> FEATURE:
<223> OTHER INFORMATION: Designed DNA based on UGT1 gene

<400> SEQUENCE: 9
tttccggtag ccatatgcac a                                       21

<210> SEQ ID NO 10
<211> LENGTH: 24
<212> TYPE: DNA
<213> ORGANISM: Artificial
<220> FEATURE:
<223> OTHER INFORMATION: Designed DNA based on UGT1 gene

<400> SEQUENCE: 10
ccgcagccca cgacctcacc tggt                                    24

-continued

```
<210> SEQ ID NO 11
<211> LENGTH: 24
<212> TYPE: DNA
<213> ORGANISM: Artificial
<220> FEATURE:
<223> OTHER INFORMATION: Designed DNA based on UGT1 gene

<400> SEQUENCE: 11
agaggaaacc aatcacgtcc aagg                                              24
```